US012721724B2

(12) United States Patent
Wengen et al.

(10) Patent No.: US 12,721,724 B2
(45) Date of Patent: Sep. 1, 2026

(54) ENHANCED SEPTUM IMPLANT HAVING A CENTRAL BRIDGE SECTION AND THREE SUBSECTIONS

(71) Applicant: Heinz Kurz GmbH, Dusslingen (DE)

(72) Inventors: Daniel Felix À Wengen, Bottmingen (CH); Thomas Stiegele, Riederich (DE); Alexander Sander, Titisee-Neustadt (DE); Matthias Mertens, Kaltenkirchen (DE)

(73) Assignee: Heinz Kurz GmbH, Dusslingen (DE)

(*) Notice: Subject to any disclaimer, the term of this patent is extended or adjusted under 35 U.S.C. 154(b) by 511 days.

(21) Appl. No.: 18/229,733

(22) Filed: Aug. 3, 2023

(65) Prior Publication Data

US 2024/0050225 A1 Feb. 15, 2024

(30) Foreign Application Priority Data

Aug. 10, 2022 (DE) ..................... 10 2022 120 193.7

(51) Int. Cl.
*A61F 2/18* (2006.01)
*A61F 2/00* (2006.01)

(52) U.S. Cl.
CPC ...... *A61F 2/186* (2013.01); *A61F 2002/0081* (2013.01); *A61F 2210/0014* (2013.01); *A61F 2230/0095* (2013.01); *A61F 2240/001* (2013.01)

(58) Field of Classification Search
CPC .................................. A61F 2/186; A61F 5/08
See application file for complete search history.

(56) References Cited

U.S. PATENT DOCUMENTS

| | | | |
|---|---|---|---|
| 5,094,233 | A | 3/1992 | Brennan |
| 5,716,405 | A | 2/1998 | Mittelman |
| 6,322,590 | B1 | 11/2001 | Sillers et al. |
| 9,895,252 | B2 | 2/2018 | Awengen et al. |
| 11,241,306 | B2 | 2/2022 | Rosenthal et al. |
| 2007/0270899 | A1 | 11/2007 | Awengen et al. |

(Continued)

FOREIGN PATENT DOCUMENTS

| | | | |
|---|---|---|---|
| CN | 215384901 U | 1/2022 | |
| CN | 114129301 A * | 3/2022 | ............. A61F 2/186 |

(Continued)

OTHER PUBLICATIONS

Translation of DE102012107123A1 (Year: 2012).*

(Continued)

*Primary Examiner* — Christie Bahena
(74) *Attorney, Agent, or Firm* — Collard & Roe, P.C.

(57) ABSTRACT

A rhinological implant for straightening the human septum has a central bridge section, which is flat or bent upward in a barrel-shaped manner, with two side sections on both sides of the bridge section, which extend upwards in a folded manner and symmetrically to the central bridge section at an angle φ of in each case about 90°, and which each have a first subsection which connects directly to the central bridge section and extends parallel thereto, a second subsection, which connects to the respective first subsection and extends at an angle relative thereto, and a third subsection that connects to an end of the respective first subsection opposite the respective second subsection, and extends also at an angle relative to the respective first subsection.

15 Claims, 3 Drawing Sheets

(56) References Cited

U.S. PATENT DOCUMENTS

| | | | | |
|---|---|---|---|---|
| 2012/0078367 | A1 | 3/2012 | Hristov et al. | |
| 2019/0374336 | A1* | 12/2019 | Zopf | A61M 27/00 |

FOREIGN PATENT DOCUMENTS

| | | | |
|---|---|---|---|
| DE | 10 2006 023 058 | B3 | 10/2007 |
| DE | 10 2012 107 123 | B4 | 3/2015 |
| EP | 1 475 056 | B1 | 10/2010 |
| EP | 2 692 313 | B1 | 4/2017 |
| WO | 2008/153263 | A1 | 12/2008 |
| WO | 2010/059586 | A1 | 5/2010 |

OTHER PUBLICATIONS

Reference [2]: Website dated Aug. 9, 2022, https://www.bess.eu/de/rhinologie/septumschienen/, with English translation, total of 5 pages.

Reference [8]: HNO. Jun. 1999; 47 (6): pp. 546-550, with English translation, total of 19 pages.

European Search Report of Application No. EP 23 18 0536 Dated Dec. 14, 2023 with English translation.

* cited by examiner 21a
20
22a
23a
23a'
22a'''
22a'
23a''
23a'''
22a''

20
23a''
23a
23a'
23a'''
26'
22a
21a 26
21a
20
22a
25'
25

21a
20
22a
23a 30
32a
31a
33a'
32a'
32a'''
33a
33a'''
33a''
32a''

30
33a
31a 32a
31a
36'
36
36'
36
36'
32a
35
35'

31a
30
32a
33a

ENHANCED SEPTUM IMPLANT HAVING A CENTRAL BRIDGE SECTION AND THREE SUBSECTIONS

CROSS REFERENCE TO RELATED APPLICATIONS

Applicant claims priority under 35 U.S.C. § 119 of German Application No. 10 2022 120 193.7 filed Aug. 10, 2022, the disclosure of which is incorporated by reference.

BACKGROUND OF THE INVENTION

1. Field of the Invention

The invention relates to a rhinological implant for straightening the nasal septum, which can be fastened on both sides of the septum of the human nose on the respective outer surface of the septum in the respective left and right side of the nasal cavity, wherein the implant has a central bridge section which is flat or curved upward very slightly from a horizontal plane at a spread angle $\omega>100°$, or is bent upward from the horizontal plane in a barrel-shaped manner at a radius of curvature $r \geq 0.5$ mm, and which, in the implanted state, encompasses the free lower edge of the septum, wherein two side sections of the implant are provided on both sides of the central bridge section and extend upwards in a folded manner and symmetrically to the central bridge section at an angle $\varphi$ of in each case about 90° against the central bridge section, and which, in the implanted state, fully abut against the two opposite outer surfaces of the septum, wherein the implant, before implantation, has been unfolded from an initially flat blank to its subsequent, implantable spatial shape, wherein the two side sections of the implant each have a first subsection which connects directly to the central bridge section and extends substantially parallel thereto, and wherein the two side sections each have a second subsection which connects to the respective first subsection and extends at an angle relative thereto.

2. The Prior Art

Such a rhinological implant for straightening the nasal septum is disclosed in the applicant's generic prior art DE 10 2012 107 123 B4≈EP 2 692 313 B1≈U.S. Pat. No. 9,895,252 B2 (=reference [1]).

In general, implants for straightening the septum are described, for example, on the website dated Aug. 9, 2022 https://www.bess.eu/de/rhinologie/septumschienen/ (=reference [2]).

Implantation of an implant, i.e., of a piece of tissue or material that is usually foreign to the body, into the human body has been long known in medical technology and is performed in numerous variations to eliminate functional disturbances of various body parts and/or mental impairments.

As is generally known, the cartilaginous portion of the human nose consists of the nasal septum (=septum), the lateral nasal cartilage and the alar cartilage. The present invention is concerned with straightening the septum. The goal of many functional but also cosmetic nasal surgeries is to straighten the septum in order to improve the air flow within the nose or simply to beautify the nose cosmetically. This process is usually accompanied by changing other structures. Currently, different suture or cartilage graft techniques are used to straighten the septum.

First, the differences between septoplasty and the columella strut technique will be explained below:

Septoplasty is aimed solely at straightening the septum and thus optimizing the supply of air via the nose. This is therefore purely functional surgery. There are a number of surgical techniques that are intended to lead to the proposed result via sutures and grafts.

Straightening a bent septum may be one of the greatest challenges in rhinoplasty. Here, different methods which essentially depend on the surgeon's experience and skill come into consideration.

Disarticulation techniques up to targeted incisions of the cartilage can play a role more or less. Those skilled in the art agree on one thing however: straightening of the septum especially in the middle arch is a difficult matter and certainly not a simple surgery.

In contrast to straightening of the septum, the columella strut technique is aimed at raising the nose tip for cosmetic reasons. In this case, a rib is pushed between the two ends of the two alar cartilages in order to raise the tip of the nose. The graft/implant is placed in a pocket between the medial borders of the alar cartilages via the spina nasalis anterior and fastened between the medial borders by deep sutures.

This is described, for example, in US 2012/0078367 A1 (=reference [3]). Here, reference is made to an implant which is biodegradable and is therefore not provided for the long term. The target region is the lower third of the nose, primarily the region around the nose tip. Although mention is made here also of connecting the implant to the septum, this is not done for straightening but for extending the septum, if the latter is short as a result of external action or from a cosmetic point of view. The bent parts of the described implant are at most about 20 mm long in their longitudinal extension, i.e., when placed on the base of the spina nasalis and the two borders of the alar cartilages, they barely reach the end of the septum. The latter is therefore never straightened. Even the seat of the implant in the implanted state would be completely unsuitable for septum straightening.

However, the implant according to reference [3] is in no way suitable for straightening the septum, and it also cannot be fastened on both sides of the septum of the human nose on the respective outer surface of the septum in the respective left and right side of the nasal cavity.

Rather, the implant according to reference [3] is a "columella strut," but not a generic septum implant according to the present invention. An aid for straightening the septum is not discussed or mentioned at all in reference [3].

WO 2008/153263 A1 (=reference [4]) also describes only techniques that are intended to raise the nose tip. Although said document also speaks of the septum and describes, for example, the technique of having to attach the implant to the upper border of the septum cartilage, this is done here, too, only for stabilizing the nasal tip implant.

The known implantation systems according to reference [3] and reference [4] thus attempt to use the end of the septum for stabilization or extension. However, none of the two systems is aimed at, or suitable for, permanently straightening the septum.

Implants for spreading the nostrils are described, for example, in U.S. Pat. No. 6,322,590 B1 (=reference [5]) or in EP 1 475 056 B1 (=reference [6]) or in DE 2006 023 058 B3 (=reference [7]). These implantation systems are also in no way designed or suitable for straightening the septum.

For straightening the septum, however, techniques with PDS films are known (described, for example, in: HNO.1999 June; 47 (6): 546-50 (=reference [8])) which are cut to size and sewn onto the septum. The razor-thin film implants are resorbed substantially without residues after 10 to 25 weeks.

More stable implants for straightening the septum are the septum rails according to Reuter that are made of silicone, as are described on the aforementioned website of the company Bess. These implants serve to splint the septum and to minimize the risk of adhesion between the septum and the lateral nasal wall after rhinoplasty. They are slotted for easier insertion and removal and have pre-punched holes for suturing.

Fluorine plastic is specified as the material. However, the rails have to be removed from the nose again after a few weeks, since silicone is not considered to be stable in the long term and potentially leads to infections.

CN 21 538 4901 U (=reference [9]) discloses a nose correction support for plastic surgery, which comprises a columella nasi support section, a nasal septum extension section, lamellas of the columella nasi support section, lamellas of the nasal septum extension section, a nose tip corner and a columella nasi with a clamping groove at the support end, a clamping groove at the head end of the septum extension and a U-shaped groove.

U.S. Pat. No. 11,241,306 B2 (=reference [10]) describes nose implants having a planar profile which has partially open spaces. Such a nose implant may be compressible along one or more dimensions, such as the width or length of the planar profile.

Compared to the prior art shown in references [2] through [10], the prior art according to reference [1] cited at the outset avoids the disadvantages of the septum rails according to Reuter, and the implant is in permanent close abutment with the septum after surgery.

The basic idea of reference [1] is to simply straighten the septum with a specially shaped and thus mechanically permanently stable structure. Here, it is important for the implant according to reference [1] to be geometrically designed such that the entire region of the septum is covered. This is achieved by the implant encompassing the free lower edge of the septum. Furthermore, both sides of the implant are perforated such that the implant can be fixed easily and securely on both sides of the septum. The thickness and associated stiffness of the implant is important in that the septum cartilage should adapt to the shape of the implant, and not vice versa.

The two side sections of the implant according to reference [1] each have a first subsection which connects directly to the central bridge section and extends substantially parallel thereto, and the two side sections each have a second subsection towards their free ends, which connects to the respective first subsection and extends at an angle relative thereto. These simple measures increase the mechanical long-term stability of the implant. In addition, the planar firm seating of the implant is improved on the two side surfaces of the septum.

A comparable geometric rule in the prior art according to references [2] to [10] is not within the functional range of the columella strut technique described therein or of nostril spreading, and therefore serves quite a different, discrete field of care.

SUMMARY OF THE INVENTION

In contrast, the object of the present invention is to modify an implant of the generic type according to reference [1] having the features defined at the outset with uncomplicated technical means such that an even better mechanical long-term stabilization of the septum is made possible and the planar firm seating of the implant on the two side surfaces of the septum is further improved. In particular, an as uniform as possible distribution of the contact forces in the implant attached to the septum is to be achieved.

This object is achieved in a surprisingly simple and cost-effective manner in that a third subsection connects in each case to an end of the respective first subsection opposite the respective second subsection, and extends also at an angle relative to the respective first subsection.

The new basic idea according to the invention is to design the implant more symmetrical in the longitudinal direction of the central bridge section and of the first subsection of the respective side section that is directly attached thereto. In particular, the newly provided third subsection distributes the contact forces of the implant more uniformly to the entire contact surface relative to the septum. A tilting moment, which can possibly occur in case of a second subsection being present only on one side, is compensated for—ideally even completely excluded—from the outset by the two-sided positioning of respective second and third subsections relative to the first subsections.

In this way, a particularly good geometric adaptation of the implant to the (normal) configuration of the human septum and particularly good contact of the implant on the outer surfaces of the same is achieved without greater manufacturing effort. In particular, no cavities are formed between the implant and the septum after surgery—neither in the region of the central bridge section nor on the side sections adjoining on both sides. Rather, the implant rests tightly against the septum over its entire surface facing the septum, which also brings about a particularly good mechanical hold of the implant on the septum.

In most current septum implants for correcting septum deviations or perforations of the septum, the implant structures are supported with cartilage.

In contrast, the implants according to reference [1] and according to the present invention have many advantages:

No cartilage must be removed from other regions (usually the rib). This reduces the operating time and there is less risk of infection.

The intervention is reproducible, standardized and can be planned when using prefabricated implants according to the invention.

It is to be expected that a stabilization made of metal will enable a significantly longer straightening than would be possible with deformable bone.

Furthermore, it is to be expected that the implant according to the invention will be much thinner than comparatively stable cartilage, which will have a positive effect on the desired air throughput.

Very particular preference is given to embodiments of the implant according to the invention, which are characterized in that the third subsection has a larger longitudinal extension projecting away from the first subsection than the second subsection.

This results in a geometry of the implant that is particularly well adapted to the anatomy of the septum.

In a further preferred embodiment of the invention, the two side sections of the implant each have a boomerang-shaped contour.

There are several options as regards the shape of the implant. In a simple embodiment, the implant can have an angular contour, in particular be curved in a V-shaped manner in the plane, wherein expediently the tip of the "V" should be somewhat rounded to avoid injuries. The implant can also have a trapezoidal shape and/or have more complicated, branched structures which can contribute to stabilization once the implant has been bent into its spatial final shape.

In advantageous variants of the invention, the bending angles of the free ends of the two side sections are designed such that, in the implanted state, the side sections are in tight spatial contact, in particular in preferably symmetrical clamping with the septum, which clamping is under tension on both sides, which contributes to a particularly good and permanent fit of the implant.

In further advantageous variants, the bridge section is constructed from webs of a mesh structure in order to provide the implant with increased flexibility through stretchability and compressibility in this region. Additionally or alternatively, in further embodiments, webs of a mesh structure can also be integrated in the side sections, which further increases the flexibility in terms of surface area.

Possible are also variants of the implant according to the invention which are characterized in that one or more spikes are incorporated into the side sections. The latter bond with the septum cartilage during implantation and thus ensure excellent and extremely durable hold of the implant.

In a class of particularly preferred embodiments, the implant can have perforations. On the one hand, this reduces the weight of the implant and, on the other hand, the amount of foreign material introduced into the human body through the implant is reduced as far as possible. In addition, the perforations help the implant to grow together with the tissue.

The perforations are preferably present both on the side sections of the implant and on the bridge section lying there between, and are formed, for example, as circular holes or as elongated holes.

The perforations further serve for secure fixation on the lateral nasal cartilage by means of a suture.

It can thus also be ensured that the cartilage tissue of the septum is sufficiently supplied with nutrients.

However, producing a permanent fastening of the implant by sewing it to the cartilage is normally time-consuming and sometimes even somewhat difficult due to the spatial conditions. Therefore, in advantageous variants of the invention, a connecting element, preferably a rivet element, which extends completely through the septum in the implanted state of the implant and connects the two side sections opposite to each other with respect to the septum, is present with which the implant can be permanently and securely fastened by means of a perforation through the septum that is easy to produce. Of course, this type of fastening can also be combined with the other types of fastening described above in order to ensure a particularly secure fit of the implant on the septum.

Very particular preference is given to developments of these embodiments in which the perforations together have a larger surface area than the fixed subsections of the side sections, which surround the perforations and are, in particular, formed in the shape of a web.

The mass and thus the weight of the implant can thus be significantly minimized.

The cartilage tissue of the septum can thus be supplied particularly well with nutrients.

For specific applications of the invention, it can be favorable if at least some of the perforations have the shape of a polyhedron or honeycomb.

This enables high stability even with low material use.

One class of embodiments of the invention is preferred in which the central bridge section is provided with perforations, and the perforations of the central bridge section together have a smaller surface area than the fixed subsections of the central bridge section surrounding the perforations.

The mass and thus the weight of the implant can thus be significantly minimized.

Moreover, this again ensures sufficient supply of cartilage tissue on the septum with nutrients.

Advantageous developments of this class of embodiments are characterized in that the perforations are formed in the shape of a slot, preferably by slots extending parallel to one another, in particular in the direction of the two side sections adjoining the central bridge section.

This, inter alia, makes it easier for the implanting surgeon to place the sutures.

In a particularly advantageous embodiment, the two side sections are designed to be exact mirror images of each other which, on the one hand, significantly simplifies production and, on the other hand, also provides for uniform force distributions from the implant to the septum comprised by the implant.

Embodiments of the implant according to the invention are preferred in which the side sections have rounded corners in order, on the one hand, to reliably prevent the implant from snagging or even skewering during implantation and, on the other hand, to rule out a risk of injury in the implanted state.

For some applications, it may be advantageous if the implant is made entirely or partially of metal. Metals and their alloys are predestined as material for surgical and orthopedic implants, which are intended to remain permanently in the body, because they have high fatigue strength and elasticity in addition to very good biocompatibility. Despite a relatively low density, implants made of such materials such as titanium or titanium compounds have excellent mechanical properties with long service life. Stainless steel is also well suited for the mentioned purposes.

Embodiments are preferred in which the implant is made of a material with a memory effect and/or superelastic properties, preferably of nitinol, so that, for example, optimal spring properties relative to the septum can be introduced through suitable thermal treatment of the implant.

For other applications, it may be advantageous if the implant is made entirely or partially of plastic, in particular of polymer material, preferably of a material with flexibility similar to the human septum, but has sufficient stiffnesses in order to straighten a curved septum in the long term, and without requiring a severing of the septum in order to bring about a weakening.

In addition to good biocompatibility of the material used itself, the implant can also have a special, body-compatible and/or germ-resistant coating.

To achieve a finely matched shape of the implant, it can expediently be produced by means of 3D printing technology and/or by means of laser technology.

In accordance with the individual requirements, however, the implant according to the invention can also be produced in machining technology, in particular by means of milling technology and/or by means of grinding technology, preferably sliding grinding, magnetic sliding grinding or satellite centrifugal grinding, and/or by means of polishing technology, preferably electropolishing, or in etching technology.

Finally, in further advantageous embodiments of the invention, the implant is manufactured by micro injection molding (MIM), which is known perse from WO 00/06327 A2, for example. In this way, it is possible to produce even very large quantities with constant dimensional accuracy in an extremely cost-effective manner, while the conventional implants are usually made by hand, such as jewelry, and therefore, on the one hand, are relatively expensive to manufacture and, on the other hand, can vary individually in terms of dimensional accuracy.

BRIEF DESCRIPTION OF THE DRAWINGS

Other objects and features of the invention will become apparent from the following detailed description considered in connection with the accompanying drawings. It is to be understood, however, that the drawings are designed as an illustration only and not as a definition of the limits of the invention.

In the drawings.

Figures 1A, 1B, 1C, 1D, 1E, 1F:
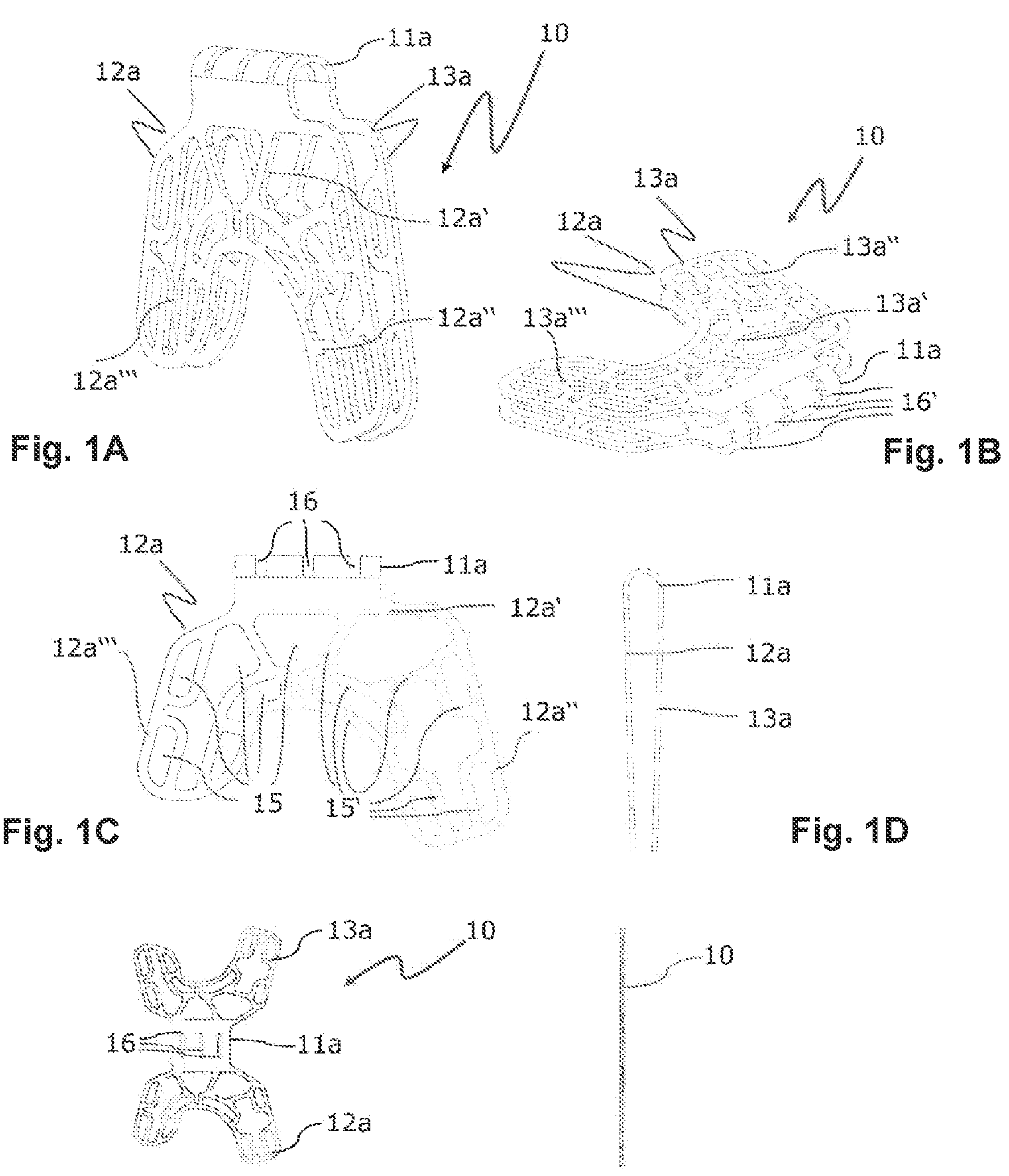
FIGS. 1A-1F show schematic, partially perspective views of an embodiment of the implant according to the invention in a small size S with a maximum total extension in a direction parallel to the axis of the central bridge section between 12 mm and 15 mm, wherein the images show the implant in different perspectives, namely.
Figures 2A, 2B, 2C, 2D:
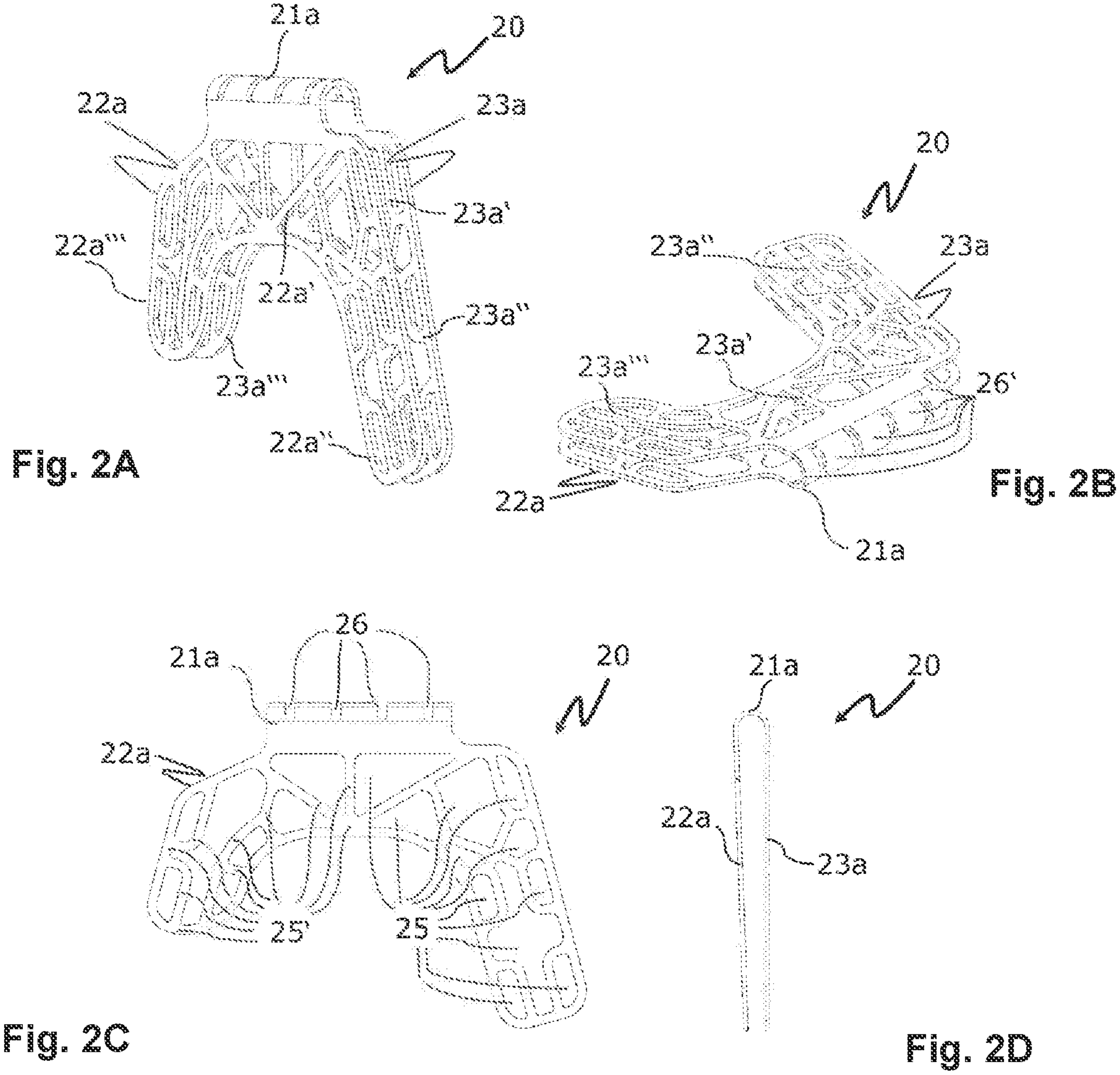
Figures 3A, 3B, 3C, 3D:
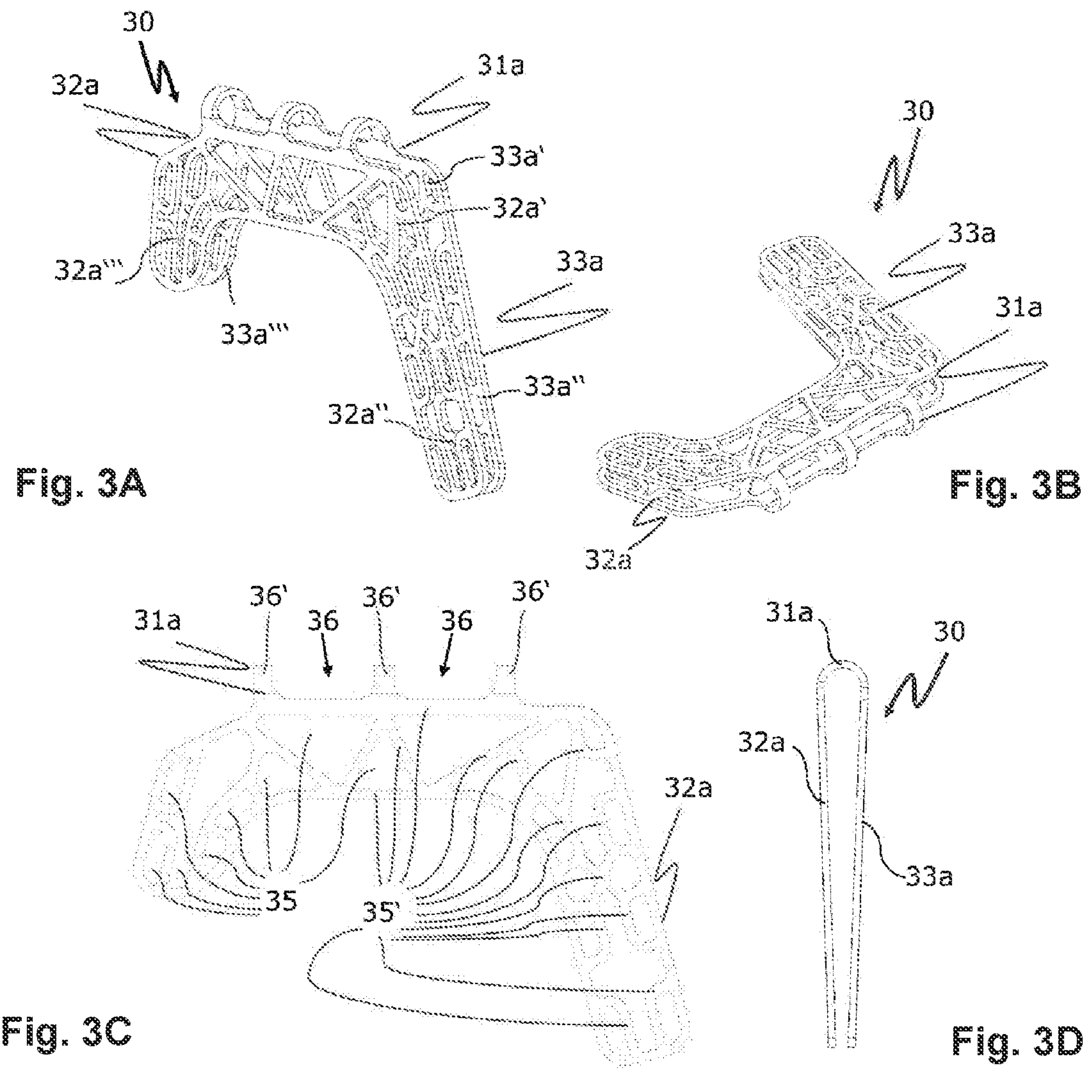

1A) spatially with viewing direction obliquely from the side,

1B) spatially lying,

1C) a side view of the implant with viewing direction, perpendicular to the plane of a side section,

1D) like C), but rotated by 90° with viewing direction parallel to the plane of the side sections,

1E) a plan view of the still flat, non-folded implant with the side sections lying in the plane of the central bridge section,

1F) like 1E), but rotated by 90° with viewing direction parallel to the plane of the side sections and of the central bridge section;

FIGS. 2A-2D like FIGS. 1A-1D, but with an embodiment of the implant according to the invention in a medium size M with a maximum total extension in a direction parallel to the axis of the central bridge section between 16 mm and 20 mm; and FIGS. 3A-3D like FIGS. 2A-2D, but with an embodiment of the implant according to the invention in a large size L with a maximum total extension in a direction parallel to the axis of the central bridge section between 20 mm and 25 mm.

DETAILED DESCRIPTION OF THE EMBODIMENTS

The rhinological implant 10; 20; 30 shown in FIGS. 1A-1E, 2A-2D and 3A-3D for straightening the septum can be fastened on both sides of the septum of the human nose on the respective outer surface of the septum in the respective left and right side of the nasal cavity. Before implantation, the implant 10; 20; 30 is unfolded from an initially flat blank to its subsequent, implantable spatial shape.

The implant 10; 20; 30 always has a central bridge section 11*a*; 21*a*; 31*a* which is flat or curved upward very slightly from a horizontal plane at a spread angle ω>100°, preferably ω>160°, or is bent upward from the horizontal plane in a barrel-shaped manner at a radius of curvature r≥0.5 mm, and which, in the implanted state, encompasses the free lower edge of the septum. Two side sections 12*a*, 13*a*; 22*a*, 23*a*; 32*a*, 33*a* are provided on both sides of the central bridge section 11*a*; 21*a*; 31*a* and extend upwards in a folded manner and symmetrically to the central bridge section 11*a*; 21*a*; 31*a* at an angle φ of in each case about 90° against the central bridge section 11*a*; 21*a*; 31*a*, and which, in the implanted state, fully abut against the two opposite outer surfaces of the septum.

In all embodiments shown in the drawing, the corners of the side sections 12*a*, 13*a*; 22*a*, 23*a*; 32*a*, 33*a* are rounded.

The two side sections 12*a*, 13*a*; 22*a*, 23*a*; 32*a*, 33*a* of the implant 10; 20; 30 each have a first subsection 12*a*', 13*a*'; 22*a*', 23*a*'; 32*a*', 33*a*' which connects directly to the central bridge section 11*a*; 21*a*; 31*a* and extends substantially parallel thereto. The two side sections 12*a*, 13*a*; 22*a*, 23*a*; 32*a*, 33*a* each have a second subsection 12*a*", 13*a*"; 22*a*", 23*a*"; 32*a*", 33*a*" towards their free ends, which connects to the respective first subsection 12*a*', 13*a*'; 22*a*', 23*a*'; 32*a*', 33*a*' and extends at an angle relative thereto. In particular, the two side sections 12*a*, 13*a*; 22*a*, 23*a*; 32*a*, 33*a* of the implant 10; 20; 30 can have an angular contour, preferably a V-shaped or boomerang-shaped contour. As a result, the mechanical long-term stability of the implant can be increased considerably and the planar firm seating on the two side surfaces of the septum can be further improved.

According to the invention, the implant 10; 20; 30 is characterized in that a third subsection 12*a*'", 13*a*'"; 22*a*'", 23*a*'"; 32*a*'", 33*a*'" connects in each case to an end of the respective first subsection 12*a*', 13*a*'; 22*a*', 23*a*'; 32*a*', 33*a*' opposite the respective second subsection 12*a*", 13*a*"; 22*a*", 23*a*"; 32*a*", 33*a*", and extends also at an angle relative to the respective first subsection 12*a*', 13*a*'; 22*a*', 23*a*'; 32*a*', 33*a*'.

The third subsection 12*a*'", 13*a*'"; 22*a*'", 23*a*'"; 32*a*'", 33*a*'" has a larger longitudinal extension projecting away from the first subsection (12*a*', 13*a*'; 22*a*', 23*a*'; 32*a*', 33*a*' than the second subsection 12*a*", 13*a*"; 22*a*", 23*a*"; 32*a*", 33*a*".

In the embodiments of the invention shown in the drawing, the two side sections 12*a*, 13*a*; 22*a*, 23*a*; 32*a*, 33*a* of the implant 10; 20; 30 are each provided with perforations 15; 25; 35 which together have a larger surface area than the, in particular web-shaped, fixed subsections 15'; 25'; 35' of the side sections 12*a*, 13*a*; 22*a*, 23*a*; 32*a*, 33*a* surrounding the perforations 15; 25; 35.

As shown in the figures of the drawing, the perforations 15; 25; 35 can have the shape of a polyhedron or honeycomb; but in an embodiment (not shown specifically) they can also be formed as circular holes or also as elongated holes. On the one hand, they help reduce the weight of the implant and, on the other hand, reduce as much as possible the amount of foreign material in the body of a patient. In addition, the perforations 15; 25; 35 help the implant 10; 20; 30 to grow together with the surrounding tissue.

The implant 10; 20; 30 is introduced into the nose by surgery during a so-called open rhinoplasty and fastened to the cartilage of the septum by means of a suture. Here, several individual sutures are applied through the perforations 15; 25; 35 and the septum, and fixed.

The central bridge section 11*a*; 21*a*; 31*a* is also preferably provided with perforations 16; 26; 36 which together have a smaller surface area than the fixed subsections 16'; 26'; 36' of the central bridge section 11*a*; 21*a*; 31*a* surrounding the perforations 16; 26; 36. The perforations 16; 26; 36 of the central bridge section 11*a*; 21*a*; 31*a* can be formed in the shape of a slot, preferably by slots extending parallel to one another, in particular in the direction of the two side sections 12*a*, 13*a*; 22*a*, 23*a*; 32*a*, 33*a* adjoining the central bridge section 11*a*; 21*a*; 31*a*.

In the embodiment of the implant 10; 20; 30 according to the invention shown in the drawing, the two side sections 12*a*, 13*a*; 22*a*, 23*a*; 32*a*, 33*a* are each designed to be exact mirror images of each other.

The implant 10; 20; 30 according to the invention can be made entirely or partially of metal, in particular of titanium, of a titanium alloy or of stainless steel and/or of a material with a memory effect and/or superelastic properties, preferably of nitinol. It will preferably have a body-compatible coating.

However, the implant 10; 20; 30 can also be made entirely or partially of plastic, in particular of polymer material, preferably of a material with flexibility similar to the human septum, but has sufficient stiffnesses in order to straighten a curved septum in the long term, and without requiring a severing of the septum in order to bring about a weakening.

The implant 10; 20; 30 can be produced by means of 3D printing technology and/or by means of laser technology. It is also possible to produce and process the implant 10; 20; 30 in machining technology, in particular by means of milling technology and/or by means of grinding technology, preferably sliding grinding, magnetic sliding grinding or satellite centrifugal grinding, and/or by means of polishing technology, preferably electropolishing, or in etching technology. Moreover, the implant 10; 20; 30 can also be manufactured by injection techniques, for example, by micro injection molding (MIM).

The purpose of the implant according to the invention is to stabilize, splint and straighten the anterior septum up to the dorsal end of the implant. Indications can be, for example, septum deviations of the anterior septum up to about 15 mm as a result of trauma, congenital deviation, etc.

In a laboratory test at the Department of Anatomy of University of Tübingen, it was tested on a body donor whether the implants according to the invention become deformed or remain stable when an external force of 20 N is applied in the implanted state. Various design variants and sizes of the septum implant according to the invention were tested. Variants that survived this test without permanent deformation, including the embodiments shown herein, were considered accepted. The three current sizes "S," "M," and "L" from pure medical grade 4 titanium with a material thickness of 0.25 mm have passed this test. A material thickness of 0.4 mm was selected for even higher safety in terms of stability. The maximum total extension in a direction parallel to the axis of the central bridge section is currently 22.6 mm for size "L" implants and 17.8 mm for size "M" implants.

Although only a few embodiments of the present invention have been shown and described, it is to be understood that many changes and modifications may be made thereunto without departing from the spirit and scope of the invention.

LIST OF REFERENCE SIGNS

10; 20; 30 rhinological implant
11*a*; 21*a*; 31*a* central bridge section
12*a*, 13*a*; 22*a*, 23*a*; 32*a*, 33*a* opposite side sections
12*a*', 13*a*'; 22*a*', 23*a*'; 32*a*', 33*a*' first subsections
12*a*'', 13*a*''; 22*a*'', 23*a*''; 32*a*'', 33*a*'' second subsections
12*a*''', 13*a*'''; 22*a*''', 23*a*'''; 32*a*''', 33*a*''' third subsections
15; 25; 35 perforations of the side sections
15'; 25'; 35' fixed subsections of the side sections
16; 26; 36 perforations of the bridge section
16'; 26'; 36' fixed subsections of the bridge section

LIST OF REFERENCES CITED IN THE SPECIFICATION

[1] DE 10 2012 107 123 B4«EP 2 692 313 B1 * U.S. Pat. No. 9,895,252 B2
[2] Website retrieved Aug. 9, 2022, https://www.bess.eu/de/rhinologie/septumschienen/
[3] US 2012/0078367 A1
[4] WO 2008/153263 A1
[5] U.S. Pat. No. 6,322,590 B1
[6] EP 1 475 056 B1
[7] DE 2006 023 058 B3
[8] HNO.1999 June; 47(6):546-50
[9] CN 21 538 4901 U
[10] U.S. Pat. No. 11,241,306 B2

What is claimed is:

1. A rhinological implant (10; 20; 30) for straightening a nasal septum of a human nose, the implant being configured to be fastened on both sides of the septum of the human nose on a respective outer surface of the septum in a respective left and right side of the nasal cavity, the implant comprising:

a central bridge section (11*a*; 21*a*; 31*a*) which is flat or curved upward from a horizontal plane at a spread angle $\omega > 100°$, or is bent upward from the horizontal plane in a barrel-shaped manner at a radius of curvature $r \geq 0.5$ mm, and which, in an implanted state, encompasses a free lower edge of the septum, two side sections (12*a*, 13*a*; 22*a*, 23*a*; 32*a*, 33*a*) disposed on both sides of the central bridge section (11*a*; 21*a*; 31*a*) and extending upwards in a folded manner and symmetrically to the central bridge section (11*a*; 21*a*; 31*a*) at an angle $\varphi$ of in each case about 90° against the central bridge section (11*a*; 21*a*; 31*a*), and which, in the implanted state, fully abut against the two opposite outer surfaces of the septum, wherein the implant (10; 20; 30), before implantation, has been unfolded from an initially flat blank to a subsequent, implantable spatial shape, wherein the two side sections (12*a*, 13*a*; 22*a*, 23*a*; 32*a*, 33*a*) of the implant (10; 20; 30) each have a first subsection (12*a*', 13*a*'; 22*a*', 23*a*'; 32*a*', 33*a*') which connects directly to the central bridge section (11*a*; 21*a*; 31*a*) and extends substantially parallel thereto, wherein the two side sections (12*a*, 13*a*; 22*a*, 23*a*; 32*a*, 33*a*) each have a second subsection (12*a*'', 13*a*''; 22*a*'', 23*a*''; 32*a*'', 33*a*'') which connects to the respective first subsection (12*a*', 13*a*'; 22*a*', 23*a*'; 32*a*', 33*a*') at a first corner and extends at an obtuse angle relative thereto, and wherein the two side sections (12*a*, 13*a*, 22*a*, 23*a*, 32*a*, 33*a*) each have a third subsection (12*a*''', 13*a*'''; 22*a*''', 23*a*'''; 32*a*''', 33*a*'''), wherein with respect to each one of the side sections (12*a*, 13*a*, 22*a*, 23*a*, 32*a*, 33*a*), the third subsection (12*a*''', 13*a*'''; 22*a*''', 23*a*'''; 32*a*''', 33*a*''') is connected at a second corner to an end of the first subsection (12*a*', 13*a*'; 22*a*', 23*a*'; 32*a*', 33*a*') opposite an end where the second subsection (12*a*'', 13*a*''; 22*a*'', 23*a*''; 32*a*'', 33*a*'') is connected to the first subsection (12*a*', 13*a*'; 22*a*', 23*a*'; 32*a*', 33*a*'), the third subsection (12*a*''', 13*a*'''; 22*a*''', 23*a*'''; 32*a*''', 33*a*''') extending at an obtuse angle relative to the first subsection (12*a*', 13*a*'; 22*a*', 23*a*'; 32*a*', 33*a*').

2. The implant according to claim 1, wherein the third subsection (12*a*''', 13*a*'''; 22*a*''', 23*a*''; 32*a*''', 33*a*''') has a larger longitudinal extension projecting away from the first subsection (12*a*', 13*a*'; 22*a*', 23*a*'; 32*a*', 33*a*') than a longitudinal extension of the second subsection (12*a*'', 13*a*''; 22*a*'', 23*a*''; 32*a*'', 33*a*'').

3. The implant according to claim 1, wherein the two side sections (12*a*, 13*a*; 22*a*, 23*a*; 32*a*, 33*a*) of the implant (10; 20; 30) each have a boomerang-shaped contour.

4. The implant according to claim 1, wherein the two side sections (12*a*, 13*a*; 22*a*, 23*a*; 32*a*, 33*a*) of the implant (10; 20; 30) are provided with perforations (15; 25; 35), and wherein the perforations (15; 25; 35) together have a larger surface area than fixed web-shaped subsections (15'; 25'; 35') of the side sections (12*a*, 13*a*; 22*a*, 23*a*; 32*a*, 33*a*) surrounding the perforations (15; 25; 35).

5. The implant according to claim 4, wherein at least some of the perforations (15; 25; 35) have the shape of a polyhedron or honeycomb.

6. The implant according to claim 1, wherein the central bridge section (11*a*; 21*a*; 31*a*) is provided with perforations (16; 26; 36), and the perforations (16; 26; 36) of the central bridge section (11*a*; 21*a*; 31*a*) together have a smaller surface area than fixed subsections (16'; 26'; 36') of the central bridge section (11*a*; 21*a*; 31*a*) surrounding the perforations (16; 26; 36).

7. The implant according to claim 6, wherein the perforations (16; 26; 36) are in the shape of slots extending parallel to one another, in a direction of the two side sections (12*a*, 13*a*; 22*a*, 23*a*; 32*a*, 33*a*) adjoining the central bridge section (11*a*; 21*a*; 31*a*).

8. The implant according to claim 1, wherein the two side sections (12*a*, 13*a*; 22*a*, 23*a*; 32*a*, 33*a*) are exact mirror images of each other.

9. The implant according to claim 1, wherein all corners of the side sections (12*a*, 13*a*; 22*a*, 23*a*; 32*a*, 33*a*) are rounded.

10. The implant according to claim 1, wherein the implant (10; 20; 30) is made of a material with a memory effect and/or superelastic properties.

11. The implant according to claim 1, wherein the implant (10; 20; 30) is made entirely or partially of plastic.

12. The implant according to claim 1, wherein the implant (10; 20; 30) has a body-compatible coating.

13. The implant according claim 1, wherein the implant (10; 20; 30) is produced by 3D printing technology and/or by laser technology.

14. The implant according to claim 1, wherein the implant (10; 20; 30) is produced using machining technology selected from the group consisting of milling technology, sliding grinding, magnetic sliding grinding, satellite centrifugal grinding, polishing technology, electropolishing and etching technology.

15. The implant according to claim 1, wherein the implant (10; 20; 30) is manufactured by micro injection molding (MIM).

* * * * *